United States Patent
Masumoto

(10) Patent No.: US 10,719,962 B2
(45) Date of Patent: Jul. 21, 2020

(54) MAGNETIC FIELD DISTORTION CALCULATION APPARATUS, METHOD, AND PROGRAM

(71) Applicant: FUJIFILM Corporation, Tokyo (JP)

(72) Inventor: Jun Masumoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 176 days.

(21) Appl. No.: 16/046,089

(22) Filed: Jul. 26, 2018

(65) Prior Publication Data

US 2019/0057525 A1    Feb. 21, 2019

(30) Foreign Application Priority Data

Aug. 17, 2017 (JP) .................................. 2017-157355

(51) Int. Cl.
*G06K 9/00* (2006.01)
*G06T 11/00* (2006.01)
(Continued)

(52) U.S. Cl.
CPC .......... *G06T 11/008* (2013.01); *A61B 5/0042* (2013.01); *A61B 5/055* (2013.01);
(Continued)

(58) Field of Classification Search
CPC .............. G01R 33/56536; G01R 33/58; G01R 33/5608; G01R 33/56563;
(Continued)

(56) References Cited

U.S. PATENT DOCUMENTS 5,005,578 A * 4/1991 Greer ................... G01R 33/565
324/318
2008/0085041 A1 4/2008 Breeuwer
(Continued)

FOREIGN PATENT DOCUMENTS

CA   2002051 A1   5/1990
JP   3-502658 A   6/1991
(Continued)

OTHER PUBLICATIONS

Bing Keong et al ("High-Field Magnetic Resonance Imaging With Reduced Field/Tissue RF Artefacts—A Modeling Study Using Hybrid MoM/FEM and FDTD Technique", IEEE vol. 48, No. 4, Nov. 2006) (Year: 2006).*

*Primary Examiner* — Amara Abdi
(74) *Attorney, Agent, or Firm* — Birch, Stewart, Kolasch & Birch, LLP

(57) ABSTRACT

In a magnetic field distortion calculation apparatus, method, and program, information of magnetic field distortion inside a subject can be accurately acquired.
An image acquisition unit acquires a reference image and a three-dimensional image of the head of the subject. A feature point detection unit detects a plurality of feature points from the three-dimensional image, and a virtual feature point estimation unit estimates a plurality of virtual feature points, which are to be present in the brain in the three-dimensional image, using the plurality of feature points. A magnetic field distortion information acquisition unit acquires magnetic field distortion information, which indicates spatial magnetic field distortion caused by a three-dimensional image capturing apparatus included in the three-dimensional image, by performing registration between the plurality of feature points and the plurality of virtual feature points and a plurality of reference points.

20 Claims, 14 Drawing Sheets

(51) Int. Cl.
| | |
|---|---|
| *G01R 33/56* | (2006.01) |
| *G06T 7/33* | (2017.01) |
| *G01R 33/565* | (2006.01) |
| *A61B 5/00* | (2006.01) |
| *A61B 5/055* | (2006.01) |
| *G01R 33/58* | (2006.01) |
| *G06T 5/00* | (2006.01) |

(52) U.S. Cl.
CPC ........ *A61B 5/7217* (2013.01); *G01R 33/5608* (2013.01); *G01R 33/56536* (2013.01); *G01R 33/56563* (2013.01); *G01R 33/58* (2013.01); *G06T 5/006* (2013.01); *G06T 7/33* (2017.01); *G06T 2207/10088* (2013.01); *G06T 2207/30016* (2013.01); *G06T 2207/30208* (2013.01)

(58) Field of Classification Search
CPC . G06T 2207/30208; G06T 2207/30016; G06T 2207/10088; G06T 11/008; G06T 5/006; G06T 7/33; A61B 5/0042; A61B 5/7217; A61B 5/055
See application file for complete search history.

(56) References Cited

U.S. PATENT DOCUMENTS

| | | | | |
|---|---|---|---|---|
| 2011/0095760 | A1* | 4/2011 | Sakakura | ............... A61B 5/055 324/309 |
| 2013/0334989 | A1* | 12/2013 | Kataoka | ............... H02N 2/0075 318/116 |
| 2017/0007148 | A1* | 1/2017 | Kaditz | ................... A61B 5/055 |
| 2017/0061588 | A1* | 3/2017 | Lee | ........................ G06T 7/248 |

FOREIGN PATENT DOCUMENTS

| | | | | |
|---|---|---|---|---|
| JP | 11-9708 | A | 1/1999 | |
| JP | 2002-34951 | A | 2/2002 | |
| JP | 2008-521471 | A | 6/2008 | |
| JP | 2012-161354 | A | 6/2012 | |
| JP | 2012161354 | * | 8/2012 | ............. A61B 5/055 |
| JP | 2017167965 | * | 9/2017 | ............. G16H 10/60 |

* cited by examiner

FIG. 12
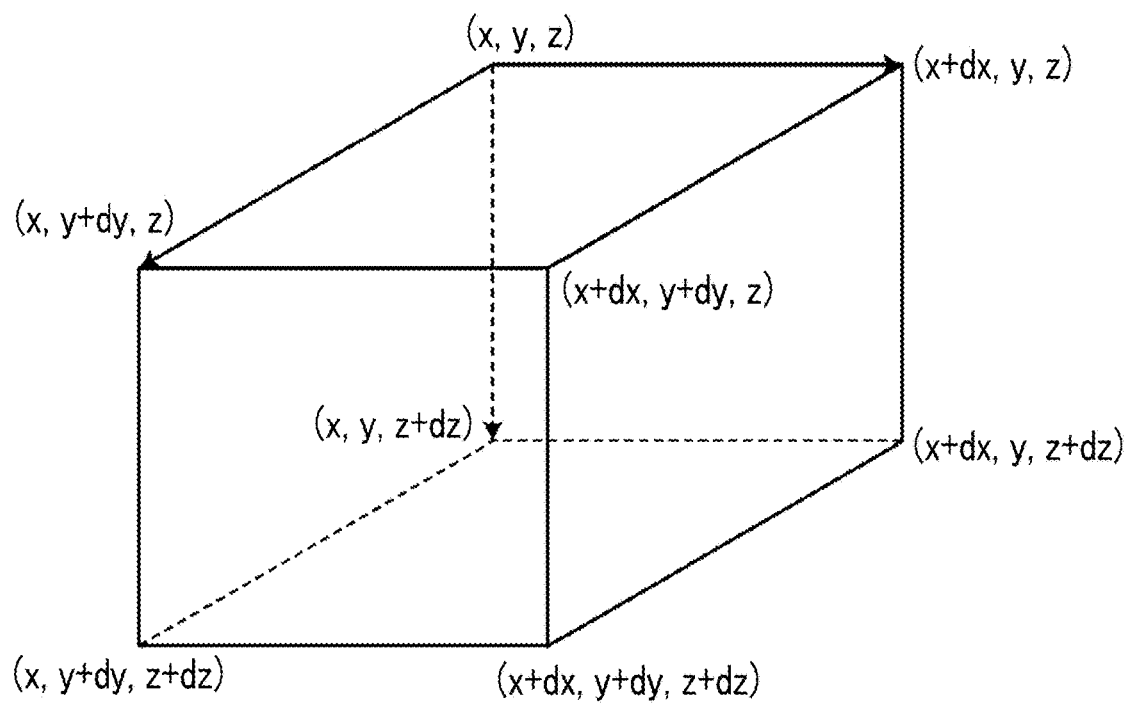
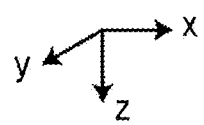

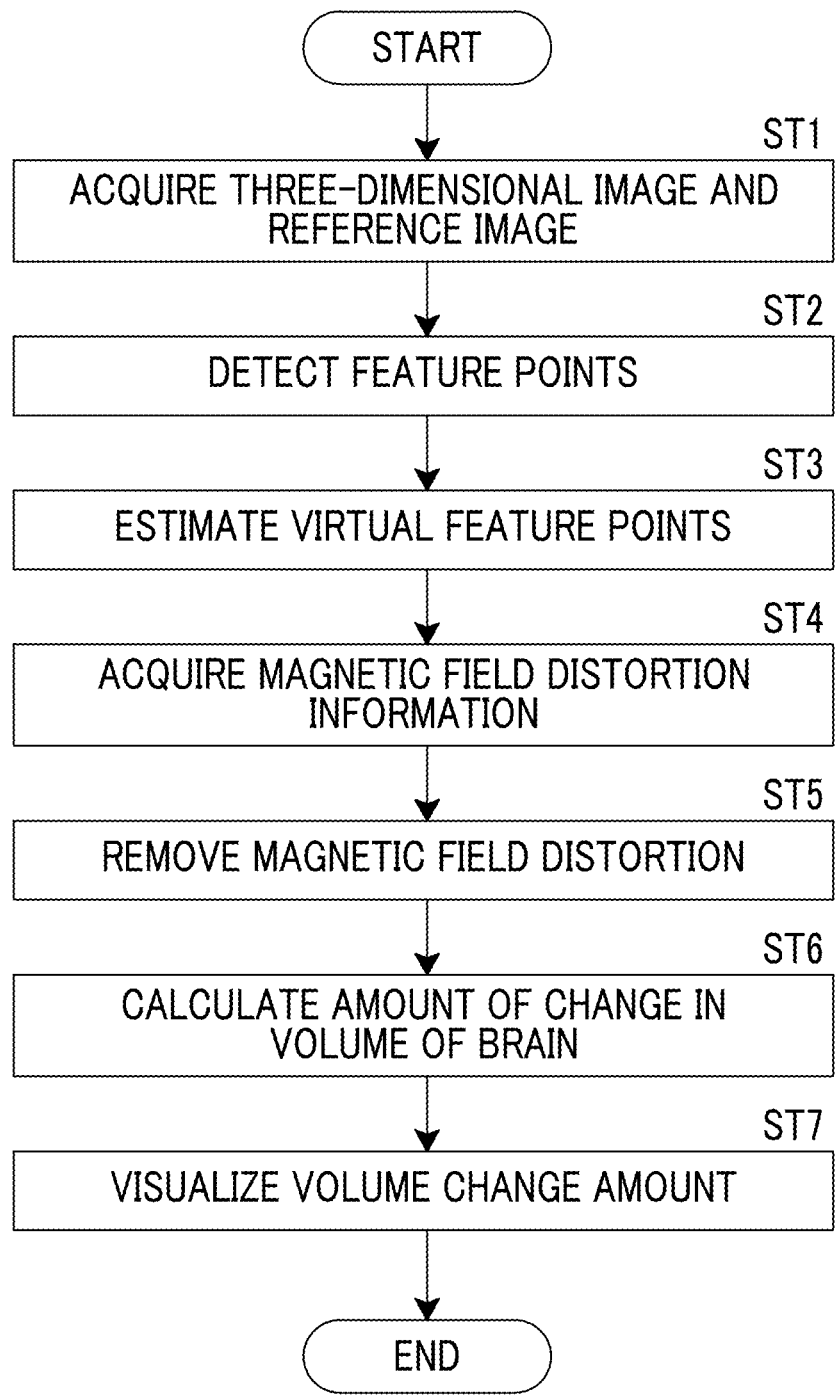

MAGNETIC FIELD DISTORTION CALCULATION APPARATUS, METHOD, AND PROGRAM

CROSS-REFERENCE TO RELATED APPLICATIONS

The present application claims priority under 35 U.S.C. § 119 to Japanese Patent Application No. 2017-157355, filed on Aug. 17, 2017, all of which are hereby expressly incorporated by reference into the present application.

BACKGROUND OF THE INVENTION

1. Field of the Invention

The present invention relates to a magnetic field distortion calculation apparatus, method, and program for calculating magnetic field distortion included in a three-dimensional image acquired by a magnetic resonance imaging (MM) apparatus.

2. Description of the Related Art

In recent years, due to advances in medical apparatuses such as computed tomography (CT) apparatuses and MRI apparatuses, high-quality three-dimensional images with high resolution are used for image diagnosis. Here, the CT apparatus can image the inside of the body of a subject in a short time. Accordingly, the CT apparatus is used for early detection of a disease and surgical planning in many cases. On the other hand, the MRI apparatus requires longer imaging time than the CT apparatus, but is advantageous in that there is no exposure to the subject. The MRI apparatus is an apparatus that images the shapes of the head, abdomen, and the like inside a human body, which is a subject, in a three-dimensional manner by applying a gradient magnetic field to the human body and measuring a nuclear magnetic resonance signal generated by atomic nuclear spins forming the tissue of the human body.

However, in the MRI image acquired by the MRI apparatus, geometric distortion due to an apparatus and geometric distortion (referred to as magnetic field distortion) due to a subject occur due to non-uniformity in a static magnetic field and incompleteness in a gradient magnetic field. Such magnetic field distortion is allowed to some extent. However, in a case where the magnetic field distortion is included in two MRI images with different imaging timings for follow-up on the same subject, it is not possible to accurately determine the progress. In particular, in a case where the subject is an Alzheimer patient, the atrophy rate of the entire brain is 1% to 3% a year, while the atrophy rate of the entire brain of a normal person is less than 1% a year. For this reason, in follow-up of Alzheimer's disease, it is necessary to accurately recognize which portion of the brain is atrophied to what extent by comparing an MRI image acquired at the time of previous diagnosis and the latest MRI image. However, in a case where magnetic field distortion is included in the MRI image, it is not possible to distinguish whether the recognized atrophy of the brain is caused by the progress of the disease or by the magnetic field distortion. For this reason, various methods for correcting the magnetic field distortion have been proposed.

For example, a method of correcting the magnetic field distortion of an MRI image by calculating a gradient magnetic field strength in an imaging cross section in the space based on the pattern of a coil forming a gradient magnetic field generator and calculating magnetic field distortion using the gradient magnetic field strength has been proposed (refer to JP2012-161354A). In addition, a method of correcting an acquired MRI image by calculating magnetic field distortion using a phantom for measuring distortion and imaging the subject using the calculated magnetic field distortion has also been proposed (refer to JP1999-9708A (JP-H11-9708A) and JP2008-521471A). By using these methods, it is possible to correct the magnetic field distortion included in the MRI image.

On the other hand, a technique of measuring magnetic field distortion using only Mill images has also been proposed. For example, JP1991-502658A (JP-H03-502658A) has proposed a method of imaging lattice members, which are regularly spaced at predetermined intervals, together with a subject and calculating distortion due to fluctuation of the magnetic field included in the captured image from the known spatial relationship for the lattice and the spatial relationship of the lattice included in the image acquired by imaging. JP2002-34951A has proposed a method of performing imaging in a state in which a ruler containing a substance, which can be clearly imaged by an MRI apparatus, at its hollow portions arranged at predetermined intervals or in predetermined shapes is placed close to a subject and acquiring information of magnetic field distortion by using the ruler included in a captured image.

SUMMARY OF THE INVENTION

On the other hand, in the MRI apparatus, magnetic field distortion may become worse due to aged deterioration of the apparatus. For this reason, in the methods disclosed in JP2012-161354A, JP1999-9708A (JP-H11-9708A), and JP2008-521471A, it is necessary to perform a calibration for measuring magnetic field distortion, for example, every predetermined period, such as half a year or one year. However, it requires very long time to measure the magnetic field distortion every predetermined period. Immediately after the calibration, the magnetic field distortion of the MRI image can be corrected with high accuracy. However, in a case where the elapsed time after the calibration is long, a possibility that the actual magnetic field distortion is different from the measured magnetic field distortion is very high. In such a case, it is not possible to accurately correct the magnetic field distortion. In the methods disclosed in JP1991-502658A (JP-H03-502658A) and JP2002-34951A, the information of magnetic field distortion can be acquired for a region where the lattice or the ruler is present. However, the information of the magnetic field distortion cannot be acquired for the inside of the subject where there is no lattice or ruler. In a case where the information of the magnetic field distortion inside the subject cannot be acquired as described above, it is not possible to correct the influence of the magnetic field distortion inside the subject. As a result, it is not possible to accurately determine the atrophy of the brain caused by Alzheimer's disease described above.

The invention has been made in view of the aforementioned circumstances, and the object of the invention is to make it possible to accurately acquire information of magnetic field distortion inside a subject.

A magnetic field distortion calculation apparatus according to the invention comprises: an image acquisition unit that acquires a medical image, which is acquired by arranging an auxiliary tool in which a plurality of marking points are arranged according to a predetermined arrangement rule around a target part of a subject and imaging the target part around which the auxiliary tool is disposed using an MRI apparatus and which includes a plurality of feature points represented by the plurality of marking points and the target part, and that acquires a reference image including a plurality of reference points arranged corresponding to the plurality of marking points according to the arrangement rule; a feature point detection unit that detects the plurality of feature points from the medical image; a virtual feature point estimation unit that estimates a plurality of virtual feature points, which are to be present in the target part in the medical image, using the plurality of feature points; and a magnetic field distortion information acquisition unit that acquires magnetic field distortion information, which indicates spatial magnetic field distortion caused by the MRI apparatus included in the medical image, by performing registration between the plurality of feature points and the plurality of virtual feature points and the plurality of reference points.

The marking points of the auxiliary tool are arranged according to the predetermined arrangement rule and are arranged around the target part of the subject. However, in a region where the target part is present, no marking point can be arranged physically. On the other hand, a plurality of reference points included in the reference image are arranged corresponding to a plurality of marking points in the auxiliary tool according to the arrangement rule. However, the reference points are also included in a region corresponding to a region where the target part of the subject is present in the auxiliary tool.

The magnetic field distortion calculation apparatus according to the invention may further comprise a distortion removal unit that removes the magnetic field distortion from the medical image based on the magnetic field distortion information.

In the magnetic field distortion calculation apparatus according to the invention, the magnetic field distortion information acquisition unit may perform rigid registration between the plurality of feature points and the plurality of virtual feature points and the plurality of reference points included in the reference image, and acquire deformation vectors between the corresponding feature points and virtual feature points and the corresponding reference points, as the magnetic field distortion information, based on the plurality of feature points and the plurality of virtual feature points and the plurality of reference points included in the reference image after the rigid registration.

The "rigid registration" is registration in a case where it is assumed that the registration target is not deformed. That is, the rigid registration does not include registration of local nonlinear deformation between three-dimensional images.

In the magnetic field distortion calculation apparatus according to the invention, the magnetic field distortion information acquisition unit may acquire the magnetic field distortion information by performing an interpolation operation, which is based on the deformation vector at each of the plurality of feature points, at positions other than the plurality of feature points and the plurality of virtual feature points in the medical image.

In the magnetic field distortion calculation apparatus according to the invention, the auxiliary tool may be formed by arranging plate-shaped members at equal intervals in three axial directions.

In the magnetic field distortion calculation apparatus according to the invention, the virtual feature point estimation unit may estimate planes corresponding to the plate-shaped members in the target part in the medical image and estimate the virtual feature points based on the estimated planes.

In the magnetic field distortion calculation apparatus according to the invention, the virtual feature point estimation unit may estimate the planes by performing a calculation for giving a larger weighting to the feature point located closer to a position to be the virtual feature point. As the calculation, for example, a least squares method can be used.

In the magnetic field distortion calculation apparatus according to the invention, the target part may be a brain.

A magnetic field distortion calculation method according to the invention comprises: acquiring a medical image, which is acquired by arranging an auxiliary tool in which a plurality of marking points are arranged according to a predetermined arrangement rule around a target part of a subject and imaging the target part around which the auxiliary tool is disposed using an MRI apparatus and which includes a plurality of feature points represented by the plurality of marking points and the target part, and acquiring a reference image including a plurality of reference points arranged corresponding to the plurality of marking points according to the arrangement rule; detecting the plurality of feature points from the medical image; estimating a plurality of virtual feature points, which are to be present in the target part in the medical image, using the plurality of feature points; and acquiring magnetic field distortion information, which indicates spatial magnetic field distortion caused by the MRI apparatus included in the medical image, by performing registration between the plurality of feature points and the plurality of virtual feature points and the plurality of reference points.

In addition, a program causing a computer to execute the magnetic field distortion calculation method according to the invention may be provided.

Another magnetic field distortion calculation apparatus according to the invention comprises: a memory that stores commands to be executed by a computer; and a processor configured to execute the stored commands. The processor executes: processing for acquiring a medical image, which is acquired by arranging an auxiliary tool in which a plurality of marking points are arranged according to a predetermined arrangement rule around a target part of a subject and imaging the target part around which the auxiliary tool is disposed using an MRI apparatus and which includes a plurality of feature points represented by the plurality of marking points and the target part, and acquiring a reference image including a plurality of reference points arranged corresponding to the plurality of marking points according to the arrangement rule; processing for detecting the plurality of feature points from the medical image; processing for estimating a plurality of virtual feature points, which are to be present in the target part in the medical image, using the plurality of feature points; and processing for acquiring magnetic field distortion information, which indicates spatial magnetic field distortion caused by the MRI apparatus included in the medical image, by performing registration between the plurality of feature points and the plurality of virtual feature points and the plurality of reference points.

According to the invention, a plurality of feature points represented by a plurality of marking points are detected from the medical image, and a plurality of virtual feature points in the target part of the subject in the medical image are estimated using the plurality of feature points. Then, information indicating spatial magnetic field distortion caused by the MRI apparatus included in the medical image is acquired by performing registration between the plurality of feature points and the plurality of virtual feature points and the plurality of reference points. For this reason, it is possible to accurately acquire information indicating the magnetic field distortion inside the target part of the subject without performing a calibration for periodically measuring the magnetic field distortion using a phantom or the like. Therefore, by using the obtained magnetic field distortion information, it is possible to accurately calculate deformation, such as the atrophy of the target part.

BRIEF DESCRIPTION OF THE DRAWINGS

FIG. 12 is a diagram illustrating the calculation of the amount of change in the volume of the brain.

FIG. 17 is a flowchart showing a process performed in the present embodiment.

DESCRIPTION OF THE PREFERRED EMBODIMENTS

Figure 1:
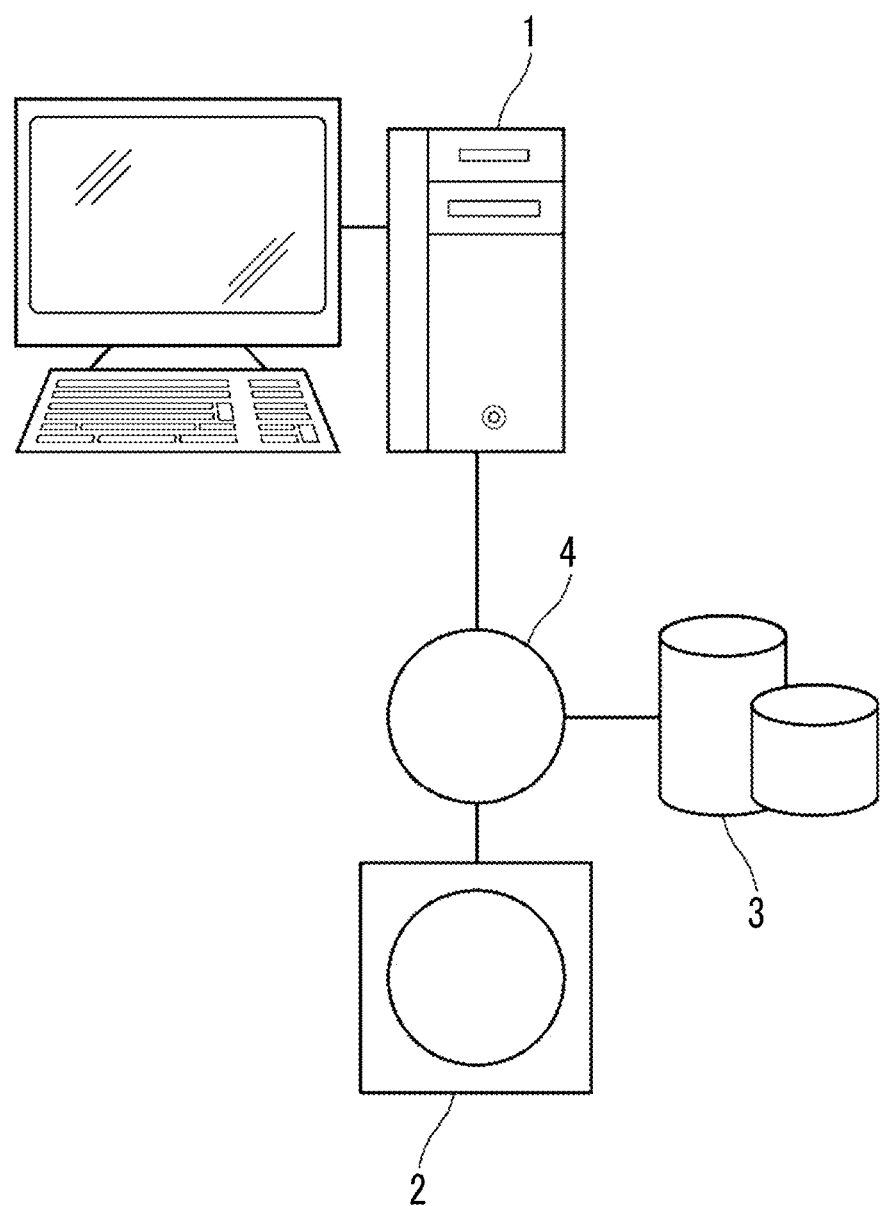
FIG. 1 is a hardware configuration diagram showing an outline of a diagnosis support system to which a magnetic field distortion calculation apparatus according to an embodiment of the invention is applied.

Hereinafter, embodiments of the invention will be described with reference to the diagrams. FIG. 1 is a hardware configuration diagram showing an outline of a diagnosis support system to which a magnetic field distortion calculation apparatus according to an embodiment of the invention is applied. As shown in FIG. 1, in the diagnosis support system, a magnetic field distortion calculation apparatus 1 according to the present embodiment, a three-dimensional image capturing apparatus 2, and an image storage server 3 are communicably connected to each other through a network 4. Then, in the diagnosis support system of the present embodiment, the magnetic field distortion calculation apparatus 1 compares two three-dimensional images with different imaging timings for comparative diagnosis of a diagnosis target part of the subject.

The three-dimensional image capturing apparatus 2 is an apparatus that generates a three-dimensional image showing a part, which is a diagnosis target part of the subject, by imaging the part. In the present embodiment, the three-dimensional image capturing apparatus 2 is an MRI apparatus. The three-dimensional image generated by the three-dimensional image capturing apparatus 2 is transmitted to the image storage server 3 and is stored therein. In the present embodiment, it is assumed that the diagnosis target part of the subject is the brain and the three-dimensional image capturing apparatus 2 generates a three-dimensional image of the head of the subject. The three-dimensional image acquired by the three-dimensional image capturing apparatus 2 corresponds to a medical image.

Here, the three-dimensional image acquired by the MRI apparatus includes magnetic field distortion. Magnetic field distortion is allowed to some extent. However, in a case where the magnetic field distortion is included in two three-dimensional images with different imaging timings, it is not possible to accurately determine the progress of the disease of the target part. In particular, in a case where the subject is an Alzheimer patient, the atrophy rate of the entire brain is 1% to 3% a year, while the atrophy rate of the entire brain of a normal person is less than 1% a year. For this reason, in follow-up of Alzheimer's disease, it is necessary to accurately recognize which portion of the brain is atrophied to what extent by comparing a three-dimensional image acquired at the time of previous diagnosis and the latest three-dimensional image. However, in a case where magnetic field distortion is included in the three-dimensional image, it is not possible to distinguish whether the recognized atrophy of the brain is caused by the progress of the disease or by the magnetic field distortion.

In the present embodiment, as will be described later, an auxiliary tool is disposed around the head of the subject to image the head of the subject. By using a three-dimensional image acquired as described above, magnetic field distortion information indicating magnetic field distortion caused by the MRI apparatus is acquired. By using the magnetic field distortion information, it is possible to determine the amount of change in the volume of the brain, that is, the degree of atrophy of the brain, without being affected by magnetic field distortion.

The image storage server 3 is a computer that stores and manages various kinds of data, and includes a large-capacity external storage device and software for database management. The image storage server 3 performs communication with other devices through the wired or wireless network 4 to transmit and receive image data or the like. Specifically, the image storage server 3 acquires image data, such as a three-dimensional image generated by the three-dimensional image capturing apparatus 2, through the network, and stores the image data in a recording medium, such as a large-capacity external storage device, and manages the image data. The storage format of image data and the communication between apparatuses through the network 4 are based on a protocol, such as a digital imaging and communication in medicine (DICOM). In the present embodiment, it is assumed that three-dimensional images of the head with different imaging timings for the same subject are stored in the image storage server 3.

The magnetic field distortion calculation apparatus 1 is realized by installing a magnetic field distortion calculation program of the invention on one computer. The computer may be a workstation or a personal computer that is directly operated by a doctor who performs diagnosis, or may be a server computer connected to these through a network. The magnetic field distortion calculation program is distributed by being recorded on a recording medium, such as a digital versatile disc (DVD) or a compact disk read only memory (CD-ROM), and is installed onto the computer from the recording medium. Alternatively, the magnetic field distortion calculation program is stored in a storage device of a server computer connected to the network or in a network storage so as to be accessible from the outside, and is downloaded and installed onto a computer used by a doctor as necessary.

Figure 2:
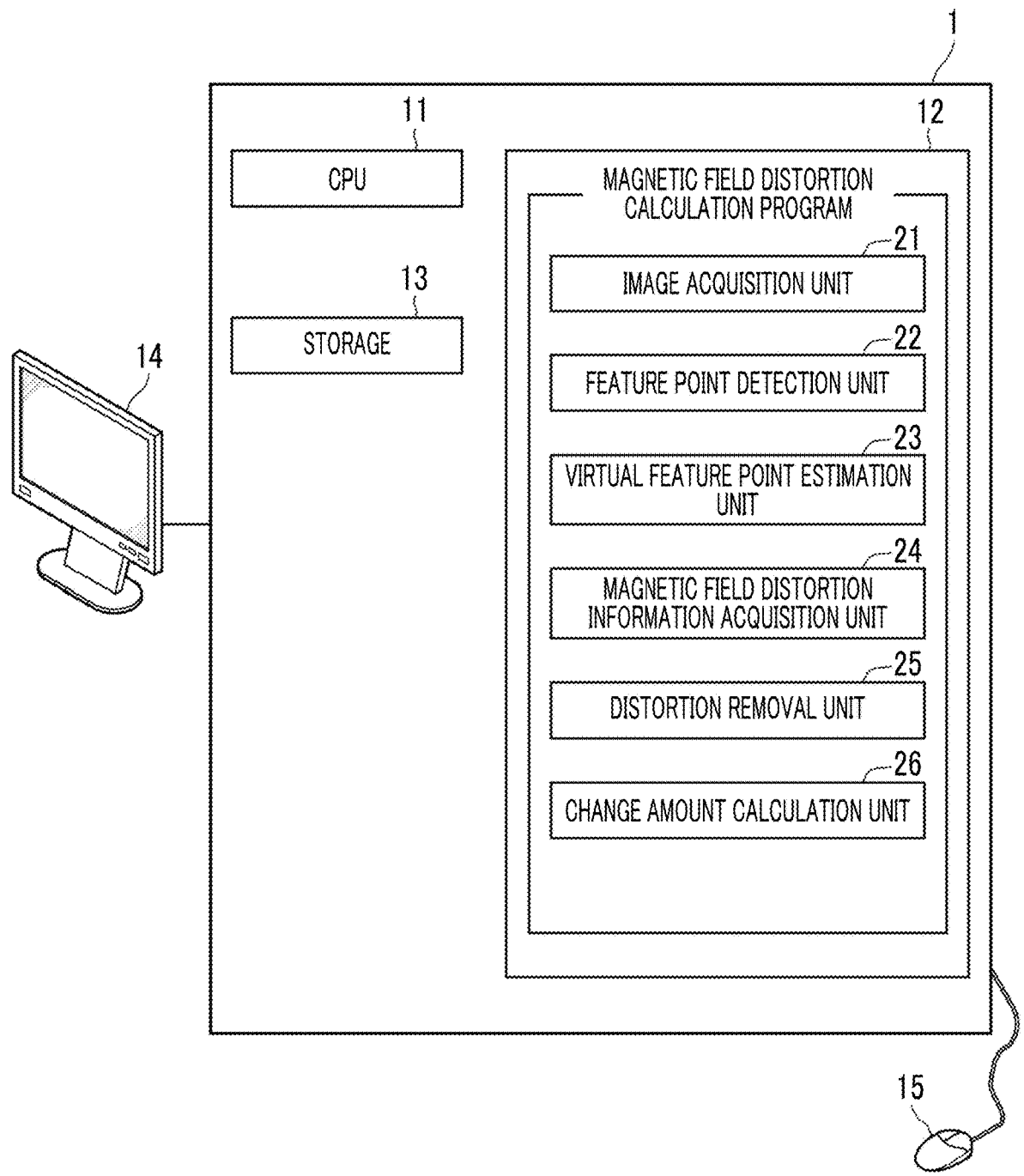
FIG. 2 is a schematic block diagram showing the configuration of the magnetic field distortion calculation apparatus according to the present embodiment.

FIG. 2 is a diagram showing the schematic configuration of the magnetic field distortion calculation apparatus realized by installing a magnetic field distortion calculation program on a computer. As shown in FIG. 2, the magnetic field distortion calculation apparatus 1 includes a central processing unit (CPU) 11, a memory 12, and a storage 13 as the configuration of a standard workstation. A display 14 and an input unit 15, such as a mouse, are connected to the magnetic field distortion calculation apparatus 1.

The storage 13 is a storage device, such as a hard disk or a solid state drive (SSD). Three-dimensional images of the head of the subject acquired from the image storage server 3 through the network 4 and various kinds of information including information necessary for processing are stored in the storage 13.

A magnetic field distortion calculation program is stored in the memory 12. A magnetic field distortion calculation program defines, as processing to be executed by the CPU 11: image acquisition processing for acquiring a reference image B0 and a three-dimensional image G1 of the head of the subject acquired by the three-dimensional image capturing apparatus 2; feature point detection processing for detecting a plurality of feature points from the three-dimensional image G1; virtual feature point estimation processing for estimating a plurality of virtual feature points, which are to be present in the brain in the three-dimensional image G1, using the plurality of feature points; magnetic field distortion information acquisition processing for acquiring magnetic field distortion information indicating spatial magnetic field distortion caused by the three-dimensional image capturing apparatus 2 included in the three-dimensional image G1 by performing registration between a plurality of feature points and a plurality of virtual feature points and a plurality of reference points included in the reference image B0; distortion removal processing for removing magnetic field distortion from the three-dimensional image G1 based on the magnetic field distortion information; and change amount calculation processing for calculating the amount of change in the volume of the brain from two three-dimensional images of the same subject.

The CPU 11 executes these processes according to the program, so that the computer functions as an image acquisition unit 21, a feature point detection unit 22, a virtual feature point estimation unit 23, a magnetic field distortion information acquisition unit 24, a distortion removal unit 25, and a change amount calculation unit 26. The magnetic field distortion calculation apparatus 1 may include a plurality of processors or processing circuits that perform image acquisition processing, feature point detection processing, virtual feature point estimation processing, magnetic field distortion information acquisition processing, distortion removal processing, and change amount calculation processing.

The image acquisition unit 21 acquires the three-dimensional image G1 of the head including the brain, which is a target part of the subject, from the image storage server 3. In a case where the three-dimensional image G1 is already stored in the storage 13, the image acquisition unit 21 may acquire the three-dimensional image G1 from the storage 13.

Figure 3:
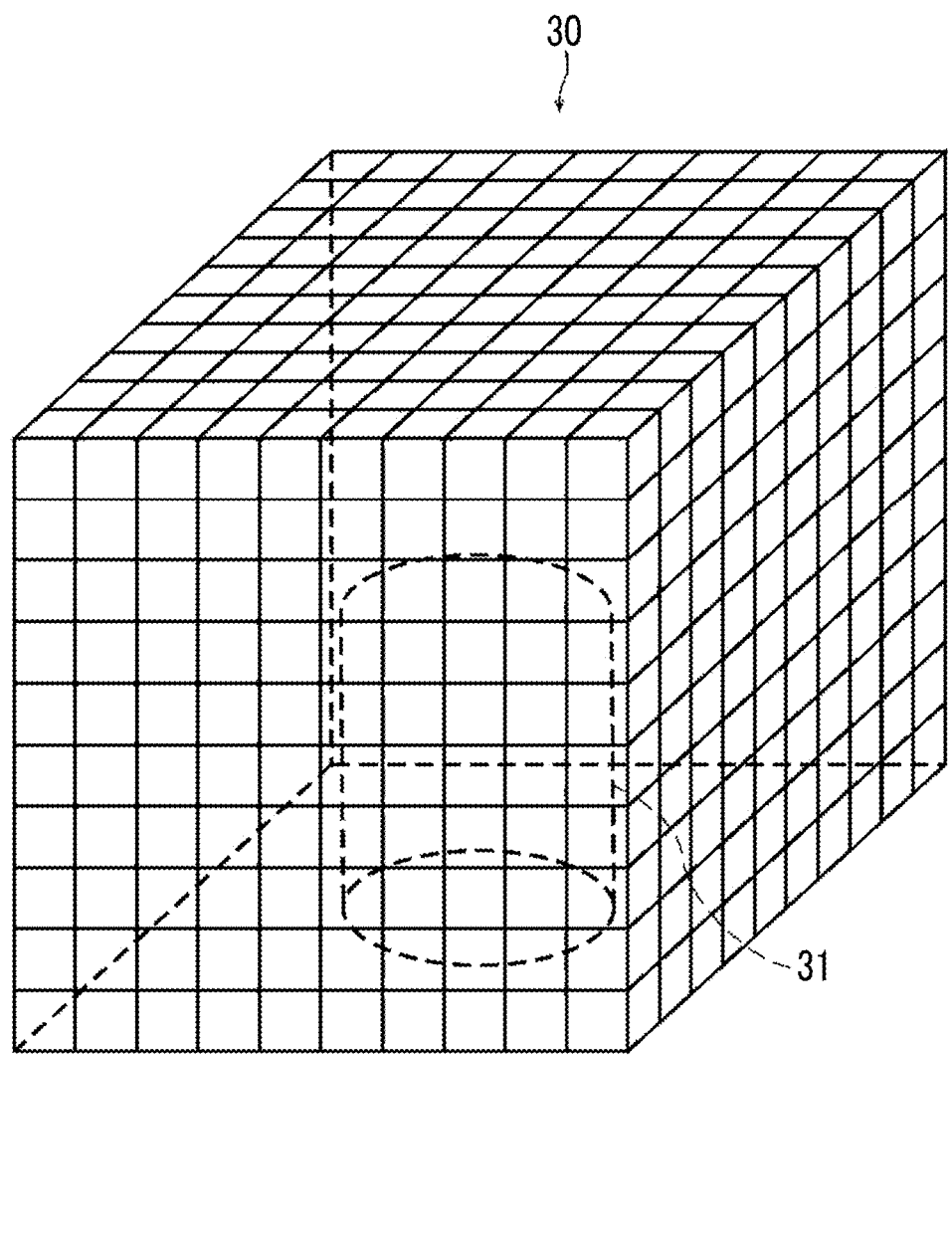
FIG. 3 is a schematic diagram showing the configuration of an auxiliary tool.

In the present embodiment, in the case of imaging the head of the subject using the three-dimensional image capturing apparatus 2, an auxiliary tool is disposed around the head. FIG. 3 is a schematic diagram showing the configuration of an auxiliary tool. As shown in FIG. 3, an auxiliary tool 30 is formed by arranging plate-shaped members in a cubic box according to a predetermined arrangement rule. In the present embodiment, the auxiliary tool 30 is formed by arranging the plate-shaped members in parallel at equal intervals in the x, y, and z directions shown in FIG. 3. In the auxiliary tool 30, intersections of the plate-shaped members in the x, y, and z directions are arranged at equal intervals in a three-dimensional space. In the present embodiment, each intersection of the plate-shaped members in the auxiliary tool 30 is referred to as a marking point.

At the time of imaging, the subject wears the auxiliary tool 30 from the head. Therefore, a space 31 into which the head is inserted is formed in the auxiliary tool 30. Since there is no plate-shaped member in the space 31, no marking point is present.

In the three-dimensional image G1 obtained by imaging the subject in a state in which the head is covered with the auxiliary tool 30, a plurality of feature points represented by a plurality of marking points in the auxiliary tool 30 are included around the head in the three-dimensional image G1.

The plate-shaped member forming the auxiliary tool 30 is formed of a material that does not affect the imaging of the MRI apparatus and makes feature points appear in the three-dimensional image G1. As such a material, for example, resin such as styrene can be used.

The image acquisition unit 21 acquires the reference image B0. The reference image B0 is a three-dimensional image including a plurality of reference points arranged corresponding to a plurality of marking points included in the auxiliary tool 30. The space 31 into which the head of the subject is inserted is formed in the auxiliary tool 30, and there is no marking point in the space 31. On the other hand, the reference image B0 includes a reference point even at a position corresponding to the space 31 of the auxiliary tool 30. For this reason, the reference image B0 includes a plurality of reference points arranged at intervals at which the plate-shaped members forming the auxiliary tool 30 are arranged. Therefore, the reference image B0 is equivalent to a three-dimensional image obtained by imaging the auxiliary tool 30 in a state where there is no magnetic field distortion to be described later.

The feature point detection unit 22 detects a plurality of feature points from the three-dimensional image G1. For the detection of a feature point, it is possible to use any method, such as a method based on template matching or a method using a discriminator machine-learned so as to detect a feature point.

Figure 4:
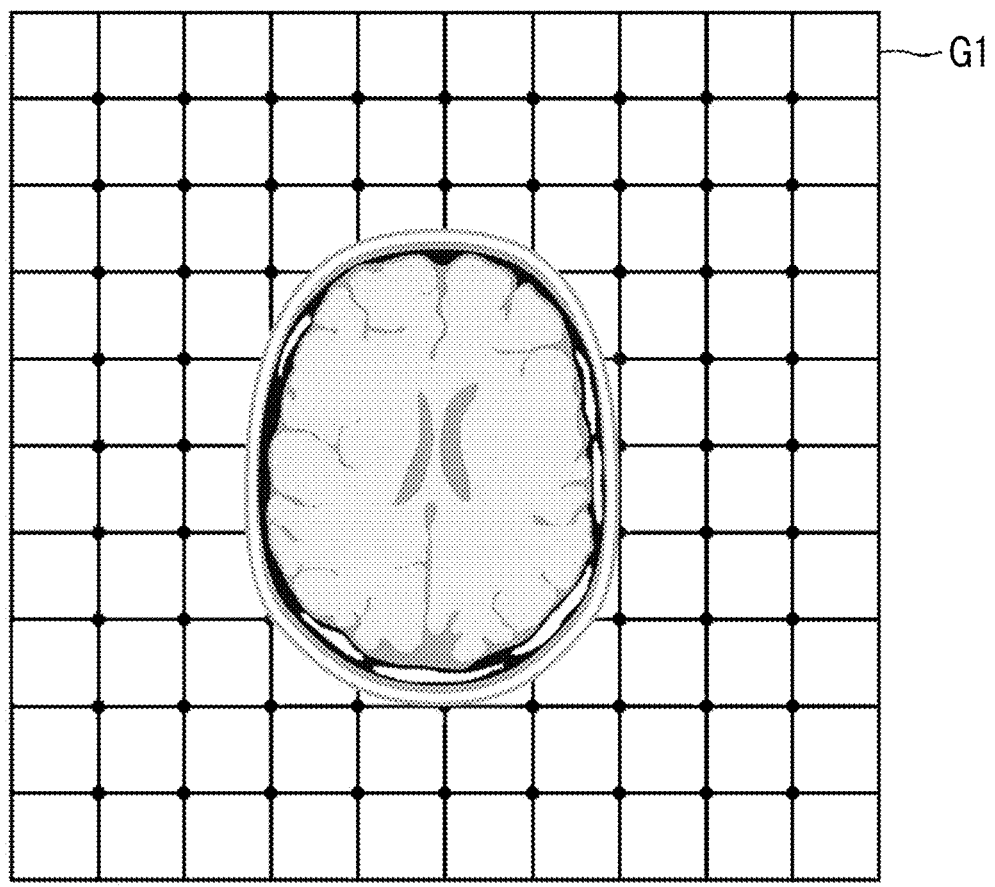
FIG. 4 is a diagram illustrating the estimation of a virtual feature point.

The virtual feature point estimation unit 23 estimates a plurality of virtual feature points, which are to be present in the brain in the three-dimensional image G1, using the plurality of feature points detected from the three-dimensional image G1 by the feature point detection unit 22. FIG. 4 is a diagram illustrating the estimation of virtual feature points. For the sake of description, FIG. 4 shows the three-dimensional image G1 as a two-dimensional image.

As shown in FIG. 4, the three-dimensional image G1 includes a plurality of feature points corresponding to a plurality of marking points included in the auxiliary tool 30. In FIG. 4, feature points are shown by black circles at intersections of the lattices. However, a plurality of feature points appear only in a region other than the brain region included in the three-dimensional image G1 but do not appear in the brain region. The virtual feature point estimation unit 23 estimates a feature point corresponding to the marking point of the auxiliary tool 30, which is to appear in the brain region, as a virtual feature point.

Figure 5:
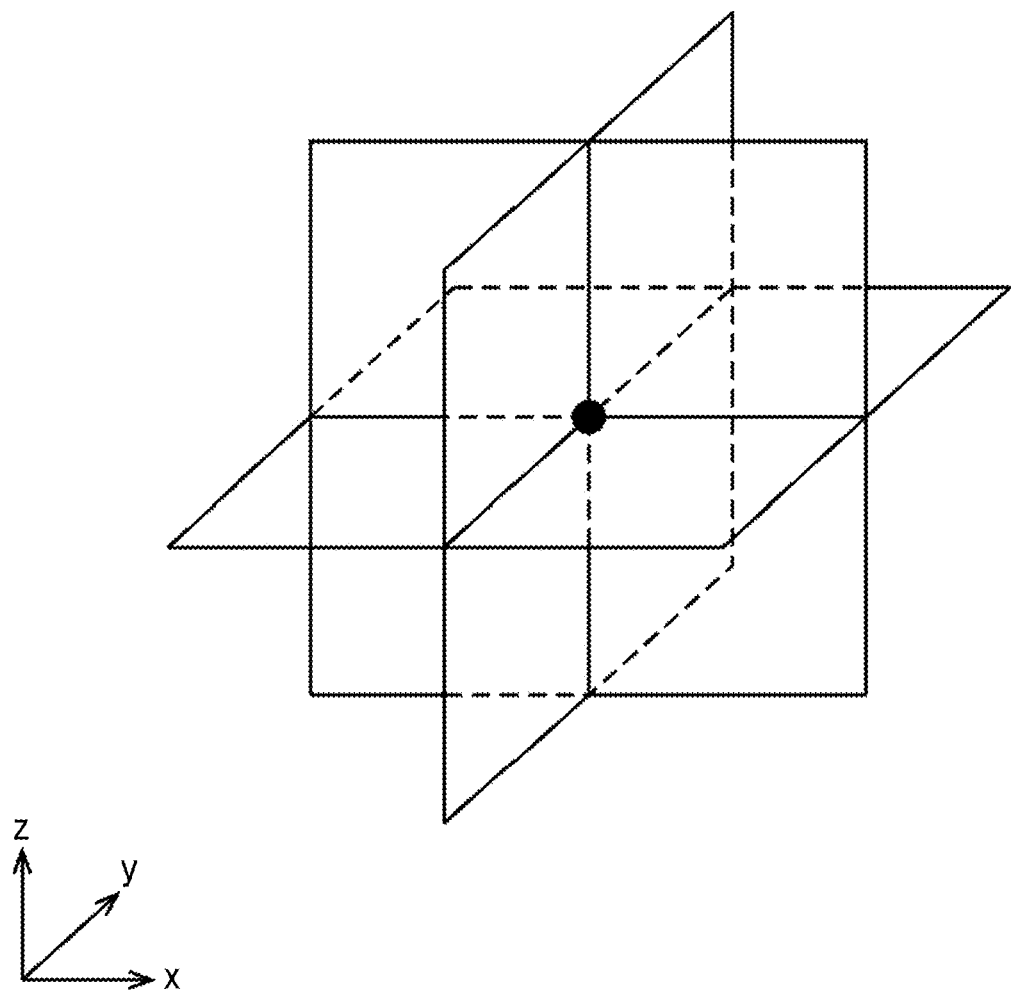
FIG. 5 is a diagram illustrating a marking point in the auxiliary tool.
Figure 6:
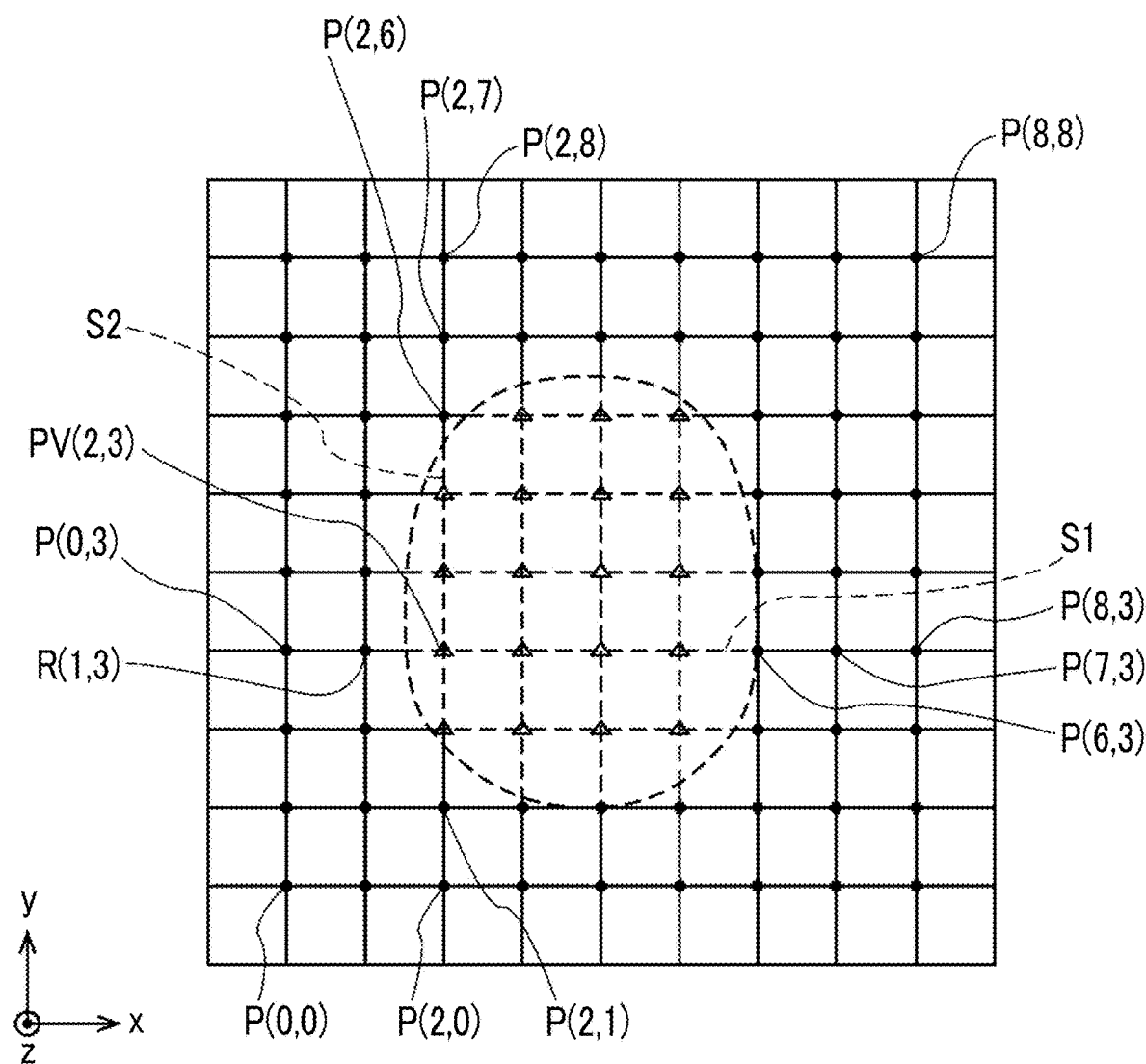
FIG. 6 is a diagram illustrating the estimation of a plane.

Here, the marking point in the auxiliary tool 30 is an intersection of three planes, as shown in FIG. 5. Therefore, in a region in the brain in the three-dimensional image G1, it is possible to estimate virtual feature points by estimating the planes in three directions in which the plate-shaped members are present in the auxiliary tool 30 and finding the intersection of the planes. FIG. 6 is a diagram illustrating the estimation of planes. The three-dimensional image G1 has three-dimensional coordinate values. However, for the sake of description, FIG. 6 shows the three-dimensional image G1 as a two-dimensional image. In FIG. 6, the outline of the brain is shown by a broken line. In FIG. 6, the coordinates of feature points and virtual feature points are expressed as xy coordinates with a feature point at the lower left corner as the origin. Therefore, the feature point at the lower left corner is expressed as a feature point P(0, 0), and the feature point at the upper right corner is expressed as a feature point P(8, 8). In FIG. 6, feature points are shown by black circles, and virtual feature points are shown by white triangles.

Here, in the three-dimensional image G1, estimation of a plane S1 parallel to the xz plane extending in the x direction shown in FIG. 6 in the brain region will be described. In order to estimate the plane S1, a least squares method using the coordinate values of feature points P(0, 3), P(1, 3), P(6, 3), P(7, 3), and P(8, 3) is used. Feature points actually used are also present in the z direction. In this case, the plane S1 is estimated by performing a calculation based on the least squares method in which a larger weighting is given to a feature point located closer to the plane S1 in the three-dimensional image G1. For example, among the three feature points P(6, 3), P(7, 3) and P(8, 3), the weighting of the feature point P(6, 3) closest to the brain is increased, and the weighting is reduced as the distance from the brain increases.

Next, estimation of a plane S2 parallel to the yz plane extending in the y direction in the brain will be described. In order to estimate the plane S2, a least squares method using the coordinate values of feature points P(2, 0), P(2, 1), P(2, 6), P(2, 7), and P(2, 8) is used. Feature points actually used are also present in the z direction. Also in this case, estimation is performed by giving a larger weighting to a feature point located closer to the plane S2 in the three-dimensional image G1. For example, among the three feature points P(2, 6), P(2, 7) and P(2, 8), the weighting of the feature point P(2, 6) closest to the brain is increased, and the weighting is reduced as the distance from the brain increases.

In a case where the planes S1 and S2 are estimated as described above, the virtual feature point estimation unit 23 finds the intersections of the planes S1 and S2 and the xy plane shown in FIG. 6. The calculated intersection is a virtual feature point PV(2, 3). Therefore, by estimating all the planes extending in the x, y, and z directions in the brain and finding the intersections of all the planes, it is possible to estimate virtual feature points in the brain region.

The magnetic field distortion information acquisition unit 24 acquires magnetic field distortion information indicating spatial magnetic field distortion caused by the three-dimensional image capturing apparatus 2 included in the three-dimensional image G1. Specifically, the magnetic field distortion information acquisition unit 24 performs rigid registration between a plurality of feature points and a plurality of virtual feature points and a plurality of reference points included in the reference image B0. Then, based on the plurality of feature points and the plurality of virtual feature points and the plurality of reference points included in the reference image B0 after the rigid registration, deformation vectors between the corresponding feature points and virtual feature points and reference points are acquired as magnetic field distortion information.

Figure 7:
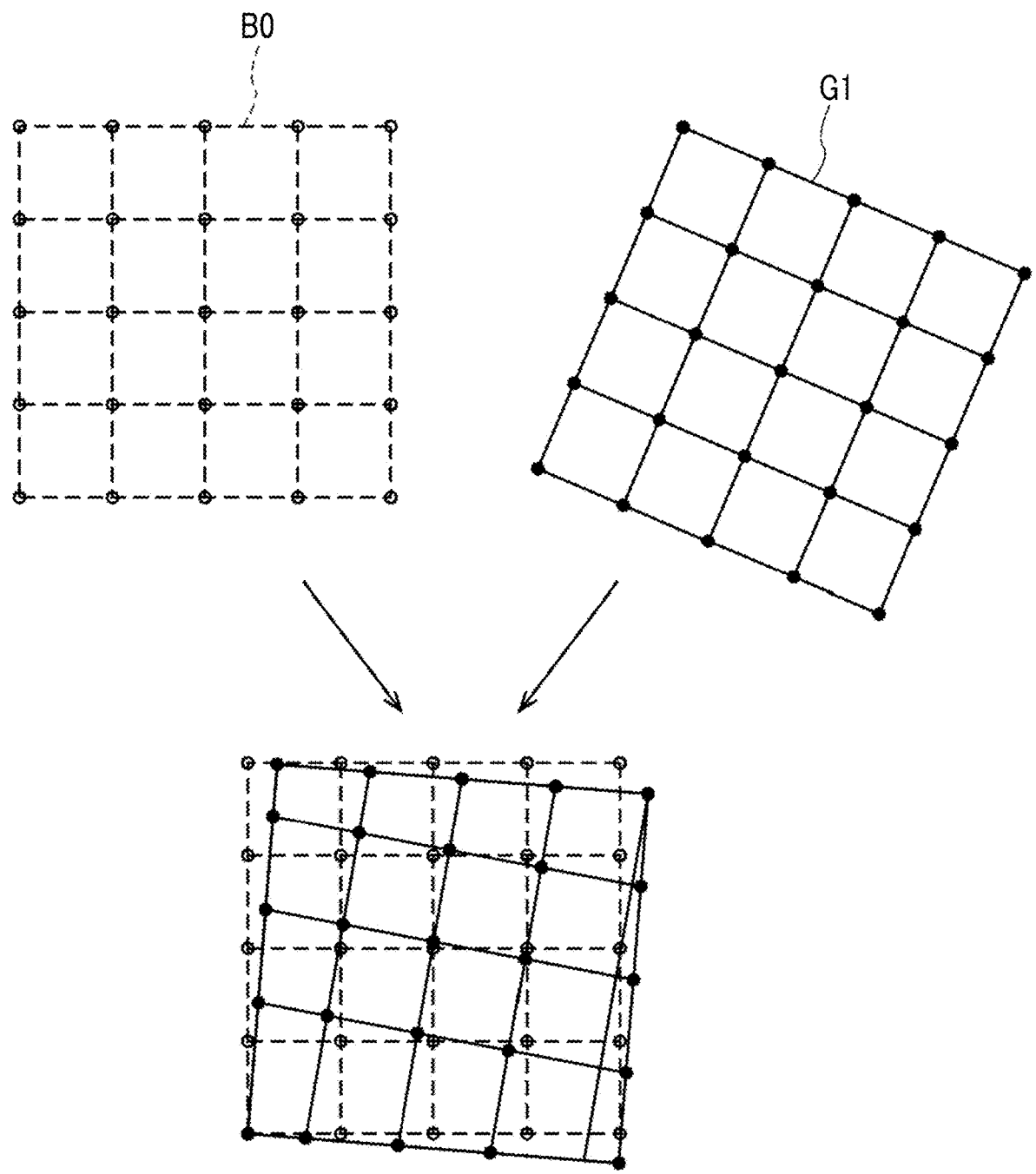
FIG. 7 is a diagram illustrating rigid registration.

FIG. 7 is a diagram illustrating rigid registration. In FIG. 7, the reference image B0 and the three-dimensional image G1 are shown as two-dimensional images for the sake of description. In practice, however, the rigid registration may be performed in the three-dimensional image. In FIG. 7, the reference points included in the reference image B0 are shown by white circles, and the reference points are connected to each other by broken lines. In addition, the feature points and the virtual feature points included in the three-dimensional image G1 are shown by black circles, and the feature points and the virtual feature points are connected to each other by solid lines.

The magnetic field distortion information acquisition unit 24 performs the rigid registration by performing parallel movement and rotation of the three-dimensional image G1 so that the correlation between the reference points included in the reference image B0 and the feature points and the virtual feature points included in the three-dimensional image G1 is maximized. The rigid registration may be performed using all the feature points and all the virtual feature points included in the three-dimensional image G1 and all the reference points included in the reference image B0. However, points to be used may be appropriately thinned out to perform the rigid registration.

In a case where there is no magnetic field distortion, the three-dimensional image G1 completely matches the reference image B0 by the rigid registration. However, due to the presence of magnetic field distortion in the three-dimensional image capturing apparatus 2, the feature points and the virtual feature points included in the three-dimensional image G1 are distorted. Therefore, as shown in FIG. 7, the feature points and the virtual feature points included in the three-dimensional image G1 do not completely match the reference points included in the reference image B0.

Figure 8:
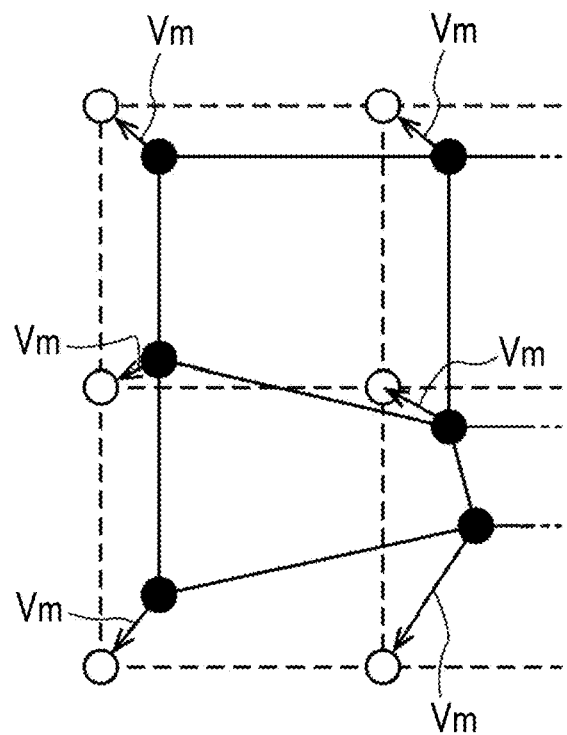
FIG. 8 is a diagram illustrating the calculation of a deformation vector.

The magnetic field distortion information acquisition unit 24 calculates deformation vectors, which are for completely matching the feature points and the virtual feature points included in the three-dimensional image G1 after the rigid registration with the reference points included in the reference image B0, as magnetic field distortion information. FIG. 8 is a diagram illustrating the calculation of a deformation vector. Also in FIG. 8, an image is shown in a two-dimensional manner, reference points included in the reference image B0 are shown by white circles, and the reference points are connected to each other by broken lines. In addition, the feature points and the virtual feature points included in the three-dimensional image G1 are shown by black circles, and the feature points and the virtual feature points are connected to each other by solid lines.

The magnetic field distortion information acquisition unit 24 performs non-rigid registration so that the three-dimensional image G1 after the rigid registration matches the reference image B0, thereby acquiring deformation vectors Vm of the feature points and the virtual feature points included in the three-dimensional image G1 with respect to the reference points of the reference image B0.

For the non-rigid registration in the present embodiment, in order to maximize or minimize a predetermined function for determining the similarity between the three-dimensional image G1 and the reference image B0 after the rigid registration, a method of calculating, as the deformation vector Vm, the amount of deformation of the feature points and the virtual feature points for matching the feature points and the virtual feature points included in the three-dimensional image G1 with the reference points of the reference image B0 is used. As examples of the non-rigid registration, it is possible to use any method, such as a method described in "Rueckert D Sonoda L I, Hayesc, Et al., "Nonrigid Registration Using Free-Form Deformations: application to breast MR Images", IEEE transactions on Medical Imaging, 1999, vol. 18, No. 8, pp. 712-721". As a result, as shown in FIG. 8, it is possible to calculate the deformation vectors Vm for matching the feature points and the virtual feature points with the corresponding reference points. Each deformation vector Vm calculated in this manner corresponds to the magnetic field distortion information indicating spatial magnetic field distortion caused by the three-dimensional image capturing apparatus 2.

Figure 9:
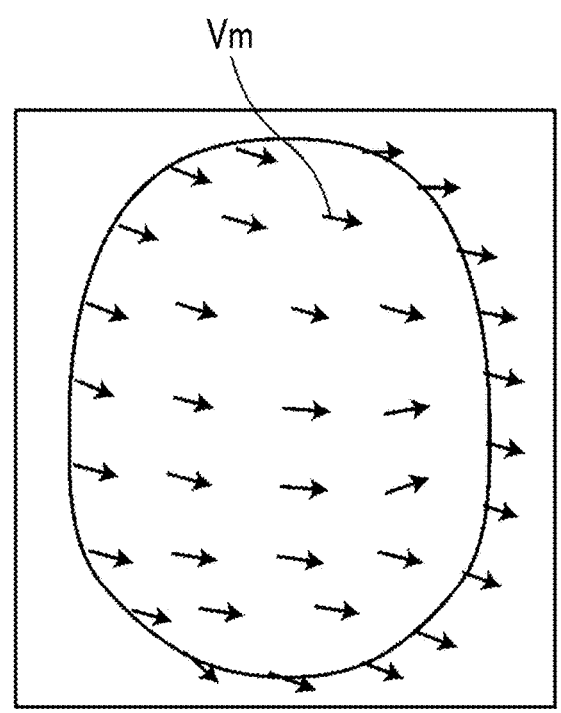
FIG. 9 is a diagram illustrating the calculation of a deformation vector in the brain region of a three-dimensional image.

The magnetic field distortion information acquisition unit 24 calculates the deformation vectors Vm at positions other than the feature points and the virtual feature points based on the deformation vectors Vm at the feature points and the virtual feature points. Specifically, by performing function fitting to a known model, such as an affine transformation model and a thin plate spline model, to spatially interpolate the deformation vectors Vm calculated at the feature points and the virtual feature points, the deformation vectors Vm at positions other than the feature points and the virtual feature points are calculated. The method of calculating the deformation vector Vm at other positions is not limited to these, and any interpolation method can be used. As a result, as shown in FIG. 9, the deformation vector Vm in the brain included in the three-dimensional image G1 is calculated as magnetic field distortion information. The deformation vector Vm calculated in this manner matches deformation due to magnetic field distortion in the brain region included in the three-dimensional image G1.

The calculation of the deformation vector Vm may be performed only for the brain region in the three-dimensional image G1, but may be performed on the entire three-dimensional image G1 including a region other than the brain region.

Figure 10:
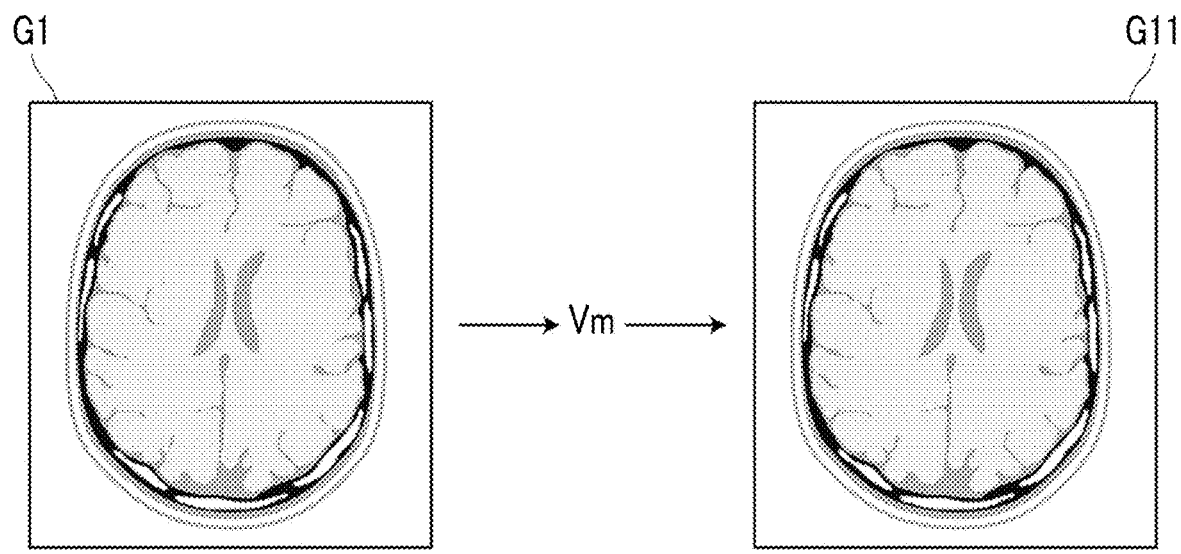
FIG. 10 is a diagram illustrating the deformation of a three-dimensional image.

The distortion removal unit 25 removes magnetic field distortion included in the three-dimensional image G1 based on the magnetic field distortion information, that is, the deformation vector Vm. Specifically, as shown in FIG. 10, by deforming the three-dimensional image G1 based on the deformation vector Vm, a three-dimensional image G11 from which magnetic field distortion has been removed is generated.

The change amount calculation unit 26 calculates the change amount of the brain using the three-dimensional image G1 (hereinafter, referred to as a first three-dimensional image) and a three-dimensional image G2 (hereinafter, referred to as a second three-dimensional image) having different imaging times for the same subject. Specifically, the change amount of the brain is calculated using the three-dimensional image G11 from which magnetic field distortion has been removed and a three-dimensional image G12 obtained by removing magnetic field distortion from the second three-dimensional image G2 in the same manner as in the three-dimensional image G1.

Figure 11:
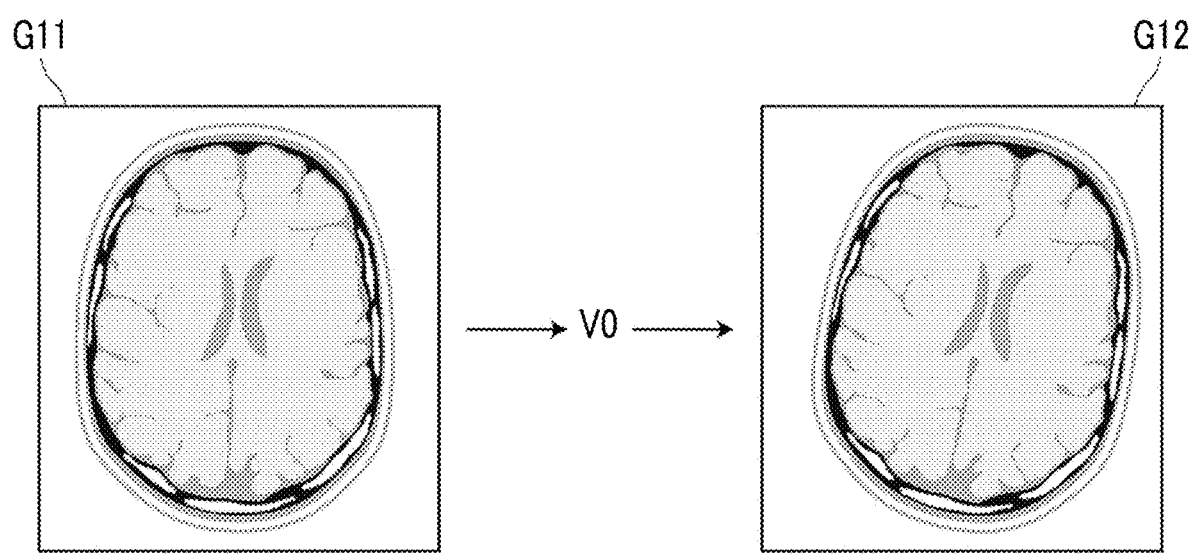
FIG. 11 is a diagram illustrating the deformation of first and second three-dimensional images.

Therefore, the change amount calculation unit 26 calculates the deformation vector V0 of each point of the brain, which is a target part included in the first three-dimensional image G11, with respect to each corresponding point of the brain included in the second three-dimensional image G12 by performing non-rigid registration between the first three-dimensional image G11 from which magnetic field distortion has been removed and the second three-dimensional image G12. Here, the deformation vector V0 represents only deformation due to atrophy of the brain due to a difference in imaging timing between the first and second three-dimensional images G1 and G2. Therefore, as shown in FIG. 11, by deforming the first three-dimensional image G11 from which magnetic field distortion has been removed using the deformation vector V0, the second three-dimensional image G12 from which magnetic field distortion has been removed is obtained.

Figure 13:
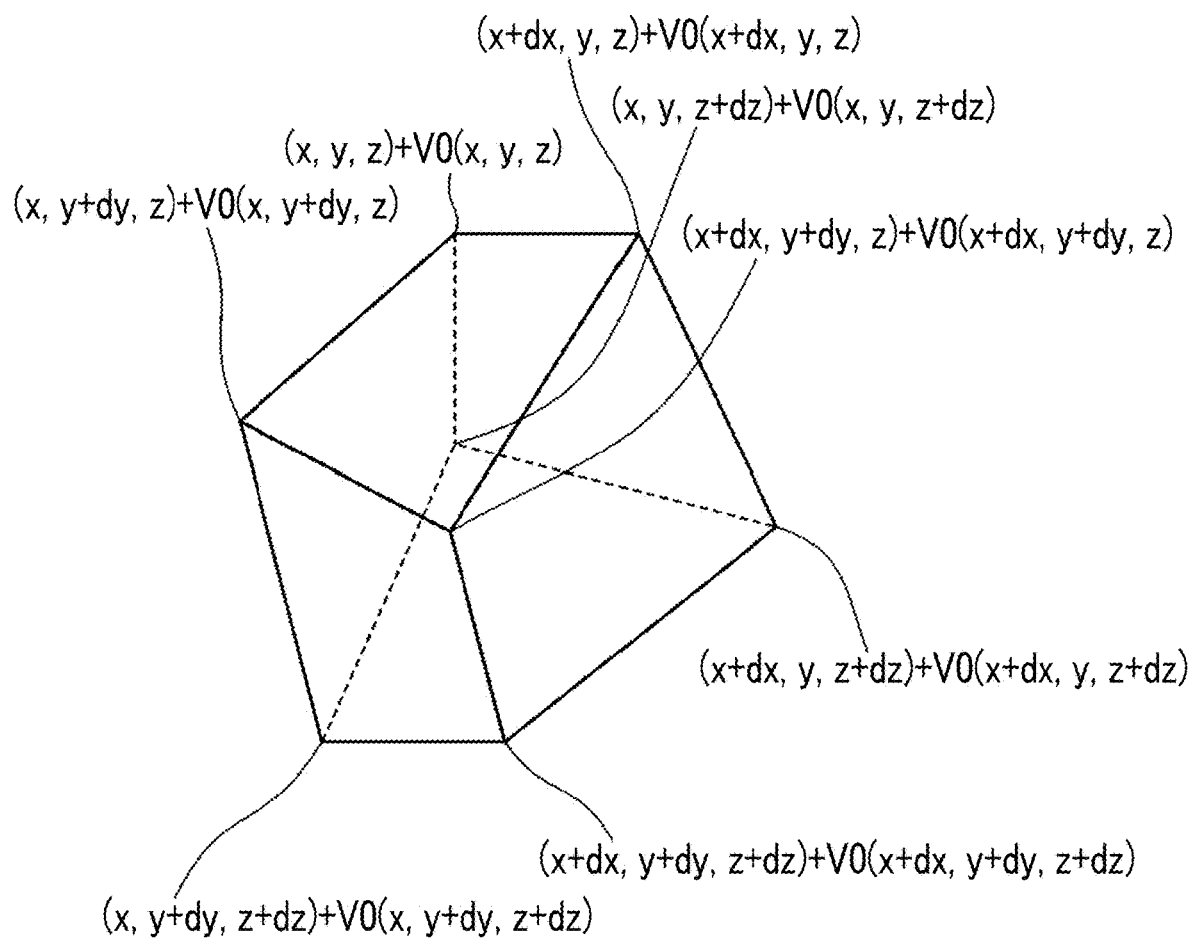
FIG. 13 is a diagram illustrating the calculation of the amount of change in the volume of the brain.

The change amount calculation unit 26 calculates the amount of change in the volume of the brain based on the deformation vector V0. Hereinafter, the calculation of the amount of change in the volume of the brain will be described. First, the change amount calculation unit 26 extracts a brain region from the first three-dimensional image G11. Then, at each pixel position in the brain region, a volume change amount is calculated. FIGS. 12 and 13 are diagrams illustrating the calculation of the amount of change in the volume of the brain. The deformation vector V0 at a certain pixel position (x, y, z) in the brain region is set to V0(x, y, z). First, a hexahedron having eight points of (x, y, z), (x+dx, y, z) (x, y+dy, z), (x, y, z+dz), (x+dx, y+dy, z), (x+dx, y, z+dz), (x, y+dy, z+dz), and (x+dx, y+dy, z+dz), which are obtained by displacing a pixel position (x, y, z) in directions of x, y, and z axes, as its apices is considered. The hexahedron is a rectangular parallelepiped, and its volume VOL1 is calculated by dx×dy×dz.

On the other hand, in a case where the above eight points are deformed by the deformation vector V0, {(x, y, z)+V0(x, y, z)}, {(x+dx, y, z)+V0(x+dx, y, z)}, {(x, y+dy, z)+V0(x, y+dy, z)}, {(x, y, z+dz)+V0(x, y, z+dz)}, {(x+dx, y+dy, z)+V0(x+dx, y+dy, z)}, {(x+dx, y, z+dz)+V0(x+dx, y, z+dz)}, {(x, y+dy, z+dz)+V0(x, y+dy, z+dz)}, and {(x+dz, y+dy, z+dz)+V0(x+dz, y+dy, z+dz)} are obtained. Accordingly, the rectangular parallelepiped shown in FIG. 12 is deformed as shown in FIG. 13, for example. The change amount calculation unit 26 calculates the volume VOL2 of the deformed hexahedron. Specifically, the change amount calculation unit 26 calculates an average value of the coordinate values of the eight pixel positions. The pixel position having the average value is a point inside deformed hexahedron. Then, a total value of the volumes of six quadrangular pyramids, each of which has the pixel position having the average value as its apex, is calculated as the volume VOL2 of the deformed hexahedron.

Then, the change amount calculation unit 26 calculates a volume change amount at each pixel position. The volume change amount is calculated by VOL2/VOL1−1. In a case where there is no change in the volume, the volume change amount is VOL2/VOL1=1. On the other hand, in a case where the volume is reduced, VOL2/VOL1 is a value smaller than 1. Accordingly, the volume change amount is a negative value. In a case where the volume is increased, VOL2/VOL1 is a value larger than 1. Accordingly, the volume change amount is a positive value. The change amount calculation unit 26 visualizes the volume change amount of each pixel position in the brain, as a brain atrophy rate, in the brain image generated from the first three-dimensional image G1, and displays it on the display 14. Hereinafter, visualization of the volume change amount will be described.

Figure 14:
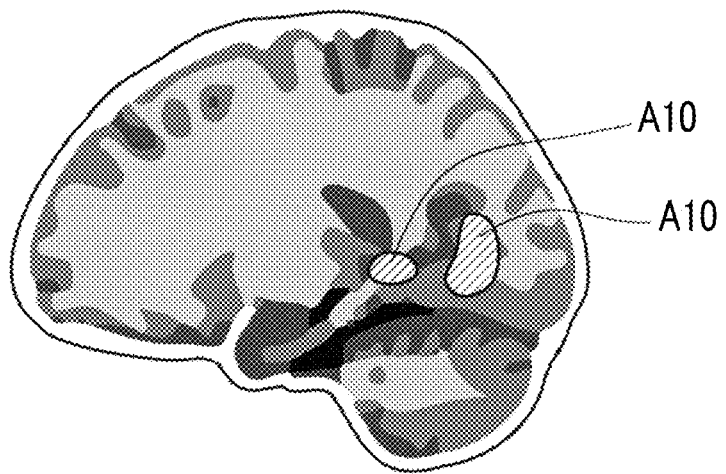
FIG. 14 is a diagram showing a state in which a volume change amount is visualized in a brain image showing the surface of the brain.

FIG. 14 is a diagram showing a state in which a volume change amount is visualized in an image showing the surface of the brain generated from the first three-dimensional image G1. FIG. 14 is a brain image of the left side surface of the brain. As shown in FIG. 14, in the brain image, a region (hereinafter, referred to as an abnormal region) A10 including a pixel position where the volume change amount exceeds ±3%, that is, a pixel position where the absolute value of the volume change amount exceeds 3%, is shown with a color different from the surface of the brain, for example, red. In FIG. 14, the color is indicated by diagonal lines. Although FIG. 14 shows an image of the left side surface of the brain, the abnormal region A10 may be visualized by displaying an image of one of the left side surface, the right side surface, the rear surface, the front surface, the top surface, and the bottom surface or a plurality of images of a plurality of surfaces among these.

Figure 15:
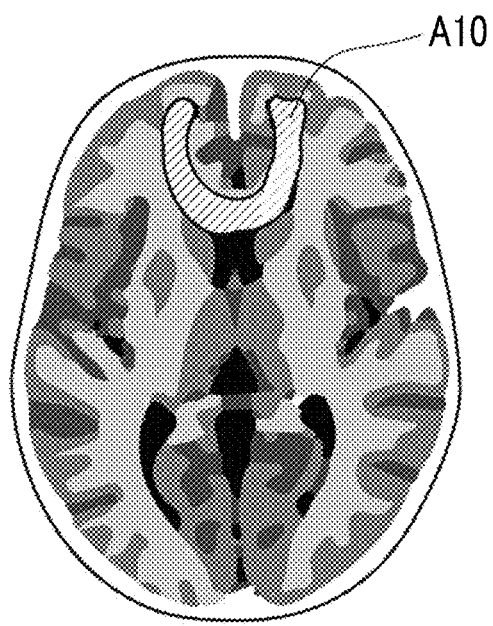
FIG. 15 is a diagram showing a state in which a volume change amount is visualized in a brain image showing the cross section of the brain.

FIG. 15 is a diagram showing a state in which a volume change amount is visualized in a brain image showing a cross section of the brain generated from the first three-dimensional image G1. As shown in FIG. 15, in the brain image of the axial cross section of the brain, an abnormal region A10 including a pixel position where the absolute value of the volume change amount exceeds 3% is shown with a color different from its surrounding, for example, red. In FIG. 15, the color is indicated by diagonal lines. The position of the displayed cross section can be changed by the operation of the operator. Although FIG. 15 shows an image of the axial cross section of the brain, the abnormal region A10 may be visualized by displaying an image of one of the axial cross section, the coronal cross section, and the sagittal section or images of a plurality of cross sections among these.

In FIGS. 14 and 15, the abnormal region A10 where the absolute value of the volume change amount exceeds 3% is visualized with one color. However, the abnormal region may be visualized with stepwise different colors according to the volume change amount. In this case, for example, the volume change amount may be visualized by using red for a region where the absolute value of the volume change amount exceeds 3%, orange for a region where the absolute value of the volume change amount is 2% or more and less than 3%, yellow for a region where the absolute value of the volume change amount is 1% or more and less than 2%, and green for a region where the absolute value of the volume change amount is less than 1%. In addition, each pixel position may be visualized with stepwise different colors according to the volume change amount. In the brain image showing the cross section of the brain, each pixel position may be visualized with stepwise different colors according to the volume change amount. In addition, a motion picture may be generated so that the cross section position is sequentially changed. Thus, the volume change amount at each position of the brain can be checked on the motion picture.

Figure 16:
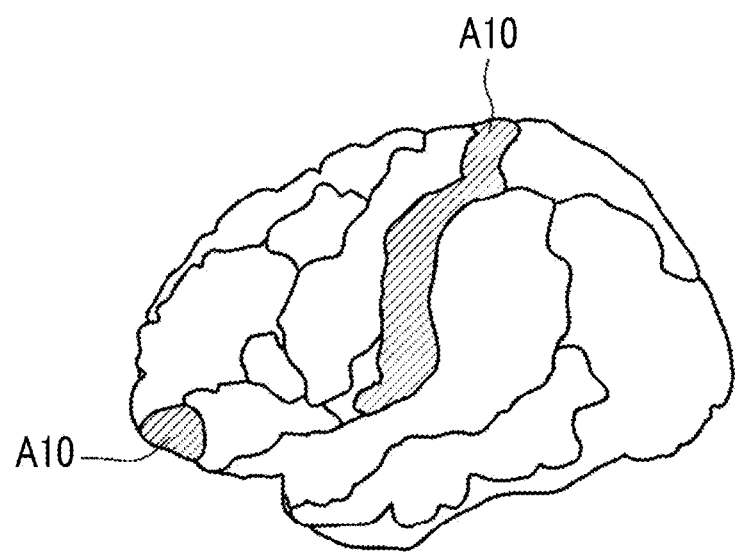
FIG. 16 is a diagram showing a state in which an abnormal region is visualized for each brain area in a brain image showing the surface of the brain.

On the other hand, in the brain, the cerebral neocortex can be anatomically divided into a plurality of brain areas. Therefore, the extracted brain may be divided into a plurality of brain areas, and the volume change amount may be calculated for each brain area. In this case, a representative value such as an average value, a maximum value, and a standard deviation of the volume change amount of each pixel position calculated in each brain area may be calculated, and a brain area where the absolute value of the representative value exceeds 3% may be visualized as the abnormal region A10 in the first three-dimensional image G1. FIG. 16 is a diagram showing a state in which the volume change amount is visualized for each brain area in a brain image showing a surface of the brain. In FIG. 16, the image showing the surface of the brain is divided into brain areas. However, a brain image showing a cross section of the brain may be divided into brain areas, and an abnormal region may be visualized for each brain area.

Next, a process performed in the present embodiment will be described. FIG. 17 is a flowchart showing the process performed in the present embodiment. For the second three-dimensional image G2, it is assumed that magnetic field distortion is removed and the three-dimensional image G12 from which the magnetic field distortion has been removed is stored in the storage 13.

First, the image acquisition unit 21 acquires the reference image B0 and the three-dimensional image G1 of the head of the subject (step ST1). Then, the feature point detection unit 22 detects a plurality of feature points from the three-dimensional image G1 (step ST2), and the virtual feature point estimation unit 23 estimates a plurality of virtual feature points, which are to be present in the brain in the three-dimensional image G1, using the plurality of feature points (step ST3). Then, the magnetic field distortion information acquisition unit 24 acquires magnetic field distortion information, which indicates spatial magnetic field distortion caused by the three-dimensional image capturing apparatus 2 included in the three-dimensional image G1, by performing registration between the plurality of feature points and the plurality of virtual feature points and the plurality of reference points (step ST4). Then, the distortion removal unit 25 removes the magnetic field distortion from the three-dimensional image G1 (step ST5).

The change amount calculation unit 26 calculates the deformation vector V0 from the three-dimensional image G11 and the three-dimensional image G12, from which magnetic field distortion has been removed, and calculates the amount of change in the volume of the brain based on the deformation vector V0 (step ST6). Then, the change amount calculation unit 26 visualizes the calculated amount of change in the volume of the brain on a brain image obtained from the three-dimensional image G1 and displays the amount on the display 14 (step ST7), and ends the process.

As described above, in the present embodiment, a plurality of feature points represented by a plurality of marking points included in the auxiliary tool 30 are detected from the three-dimensional image G1, and a plurality of virtual feature points in the brain of the subject in the three-dimensional image G1 are estimated using the plurality of feature points. Then, information indicating spatial magnetic field distortion caused by the MRI apparatus included in the three-dimensional image G1 is acquired by performing registration between the plurality of feature points and the plurality of virtual feature points and the plurality of reference points included in the reference image B0. For this reason, it is possible to accurately acquire information indicating the magnetic field distortion in the brain of the subject without performing a calibration for periodically measuring the magnetic field distortion using a phantom or the like. Therefore, by using the obtained magnetic field distortion information, it is possible to accurately calculate deformation, such as the atrophy of the brain.

In the embodiment described above, the change amount calculation unit 26 calculates the amount of change in the volume of the brain based on the deformation vector V0.

However, without calculating the deformation vector V0, the volume of the brain in the first three-dimensional image G11 after removing the magnetic field distortion and the volume of the brain in the second three-dimensional image G2 may be calculated from the number of voxels of each image, and the difference between the volumes may be calculated as the volume change amount.

In the embodiment described above, the auxiliary tool 30 is formed by arranging the plate-shaped members at equal intervals. However, as long as marking points are arranged according to a predetermined arrangement rule, any auxiliary tool may be used.

EXPLANATION OF REFERENCES

1: magnetic field distortion calculation apparatus
2: three-dimensional image capturing apparatus
3: image storage server
4: network
11: CPU
12: memory
13: storage
14: display
15: input unit
21: image acquisition unit
22: feature point detection unit
23: virtual feature point estimation unit
24: magnetic field distortion information acquisition unit
25: distortion removal unit
26: change amount calculation unit
30: auxiliary tool
31: space
A10: abnormal region
B0: reference image
G1, G2: three-dimensional image
G11, G12: three-dimensional image from which magnetic field distortion has been removed
P: feature point
PV: virtual feature point
S1, S2: plane
V0, Vm: deformation vector

What is claimed is:

1. A magnetic field distortion calculation apparatus, comprising:
   a processor configured to
   acquire a medical image, which is acquired by arranging an auxiliary tool in which a plurality of marking points are arranged according to a predetermined arrangement rule around a target part of a subject and imaging the target part around which the auxiliary tool is disposed using an MRI apparatus and which includes a plurality of feature points represented by the plurality of marking points and the target part,
   acquire a reference image including a plurality of reference points arranged corresponding to the plurality of marking points according to the arrangement rule;
   detect the plurality of feature points from the medical image;
   estimate a plurality of virtual feature points, which are to be present in the target part in the medical image, using the plurality of feature points; and
   acquire magnetic field distortion information, which indicates spatial magnetic field distortion caused by the MRI apparatus included in the medical image, by performing registration between the plurality of feature points and the plurality of virtual feature points and the plurality of reference points.

2. The magnetic field distortion calculation apparatus according to claim 1, wherein the processor further configured to
   remove the magnetic field distortion from the medical image based on the magnetic field distortion information.

3. The magnetic field distortion calculation apparatus according to claim 1,
   wherein the processor configured to perform rigid registration between the plurality of feature points and the plurality of virtual feature points and the plurality of reference points included in the reference image, and
   acquire deformation vectors between the corresponding feature points and virtual feature points and the corresponding reference points, as the magnetic field distortion information, based on the plurality of feature points and the plurality of virtual feature points and the plurality of reference points included in the reference image after the rigid registration.

4. The magnetic field distortion calculation apparatus according to claim 2,
   wherein the processor configured to:
   perform rigid registration between the plurality of feature points and the plurality of virtual feature points and the plurality of reference points included in the reference image, and
   acquire deformation vectors between the corresponding feature points and virtual feature points and the corresponding reference points, as the magnetic field distortion information, based on the plurality of feature points and the plurality of virtual feature points and the plurality of reference points included in the reference image after the rigid registration.

5. The magnetic field distortion calculation apparatus according to claim 3,
   wherein the processor configured to acquire the magnetic field distortion information by performing an interpolation operation, which is based on the deformation vector at each of the plurality of feature points, at positions other than the plurality of feature points and the plurality of virtual feature points in the medical image.

6. The magnetic field distortion calculation apparatus according to claim 1,
   wherein the auxiliary tool is formed by arranging plate-shaped members at equal intervals in three axial directions.

7. The magnetic field distortion calculation apparatus according to claim 2,
   wherein the auxiliary tool is formed by arranging plate-shaped members at equal intervals in three axial directions.

8. The magnetic field distortion calculation apparatus according to claim 3,
   wherein the auxiliary tool is formed by arranging plate-shaped members at equal intervals in three axial directions.

9. The magnetic field distortion calculation apparatus according to claim 4,
   wherein the auxiliary tool is formed by arranging plate-shaped members at equal intervals in three axial directions.

10. The magnetic field distortion calculation apparatus according to claim 6,
    wherein the processor configured to estimate planes corresponding to the plate-shaped members in the target part in the medical image, and estimates the virtual feature points based on the estimated planes.

11. The magnetic field distortion calculation apparatus according to claim 10,
wherein the processor configured to estimate the planes by performing a calculation for giving a larger weighting to the feature point located closer to a position to be the virtual feature point.

12. The magnetic field distortion calculation apparatus according to claim 1,
wherein the target part is a brain.

13. The magnetic field distortion calculation apparatus according to claim 2,
wherein the target part is a brain.

14. The magnetic field distortion calculation apparatus according to claim 3,
wherein the target part is a brain.

15. The magnetic field distortion calculation apparatus according to claim 4,
wherein the target part is a brain.

16. The magnetic field distortion calculation apparatus according to claim 5,
wherein the target part is a brain.

17. The magnetic field distortion calculation apparatus according to claim 6,
wherein the target part is a brain.

18. A magnetic field distortion calculation method, comprising:
acquiring a medical image, which is acquired by arranging an auxiliary tool in which a plurality of marking points are arranged according to a predetermined arrangement rule around a target part of a subject and imaging the target part around which the auxiliary tool is disposed using an MRI apparatus and which includes a plurality of feature points represented by the plurality of marking points and the target part, and acquiring a reference image including a plurality of reference points arranged corresponding to the plurality of marking points according to the arrangement rule;
detecting the plurality of feature points from the medical image;
estimating a plurality of virtual feature points, which are to be present in the target part in the medical image, using the plurality of feature points; and
acquiring magnetic field distortion information, which indicates spatial magnetic field distortion caused by the MRI apparatus included in the medical image, by performing registration between the plurality of feature points and the plurality of virtual feature points and the plurality of reference points.

19. A non-transitory computer readable recording medium storing a magnetic field distortion calculation program causing a computer to execute:

a step of acquiring a medical image, which is acquired by arranging an auxiliary tool in which a plurality of marking points are arranged according to a predetermined arrangement rule around a target part of a subject and imaging the target part around which the auxiliary tool is disposed using an MRI apparatus and which includes a plurality of feature points represented by the plurality of marking points and the target part, and acquiring a reference image including a plurality of reference points arranged corresponding to the plurality of marking points according to the arrangement rule;
a step of detecting the plurality of feature points from the medical image;
a step of estimating a plurality of virtual feature points, which are to be present in the target part in the medical image, using the plurality of feature points; and
a step of acquiring magnetic field distortion information, which indicates spatial magnetic field distortion caused by the MRI apparatus included in the medical image, by performing registration between the plurality of feature points and the plurality of virtual feature points and the plurality of reference points.

20. A magnetic field distortion calculation apparatus, comprising:
a memory that stores commands to be executed by a computer; and
a processor configured to execute the stored commands; and
wherein the processor executes,
processing for acquiring a medical image, which is acquired by arranging an auxiliary tool in which a plurality of marking points are arranged according to a predetermined arrangement rule around a target part of a subject and imaging the target part around which the auxiliary tool is disposed using an MRI apparatus and which includes a plurality of feature points represented by the plurality of marking points and the target part, and acquiring a reference image including a plurality of reference points arranged corresponding to the plurality of marking points according to the arrangement rule;
processing for detecting the plurality of feature points from the medical image;
processing for estimating a plurality of virtual feature points, which are to be present in the target part in the medical image, using the plurality of feature points; and
processing for acquiring magnetic field distortion information, which indicates spatial magnetic field distortion caused by the MRI apparatus included in the medical image, by performing registration between the plurality of feature points and the plurality of virtual feature points and the plurality of reference points.

* * * * *